(12) United States Patent
Akita et al.

(10) Patent No.: US 9,549,673 B2
(45) Date of Patent: Jan. 24, 2017

(54) SCANNING LASER OPHTHALMOSCOPE

(71) Applicant: NIDEK CO., LTD., Aichi (JP)

(72) Inventors: Junichi Akita, Aichi (JP); Hiroyoshi Nakanishi, Aichi (JP)

(73) Assignee: NIDEK CO., LTD., Aichi (JP)

( * ) Notice: Subject to any disclaimer, the term of this patent is extended or adjusted under 35 U.S.C. 154(b) by 0 days.

(21) Appl. No.: 14/849,791

(22) Filed: Sep. 10, 2015

(65) Prior Publication Data

US 2016/0073876 A1    Mar. 17, 2016

(30) Foreign Application Priority Data

Sep. 12, 2014   (JP) ................................. 2014-186906

(51) Int. Cl.
| | | |
|---|---|---|
| A61B 3/14 | (2006.01) | |
| A61B 3/12 | (2006.01) | |
| A61B 3/10 | (2006.01) | |
| A61B 3/00 | (2006.01) | |
| G02B 27/14 | (2006.01) | |

(52) U.S. Cl.
CPC ........... *A61B 3/1241* (2013.01); *A61B 3/0025* (2013.01); *A61B 3/0058* (2013.01); *A61B 3/10* (2013.01); *A61B 3/1025* (2013.01); *A61B 3/14* (2013.01); *G02B 27/141* (2013.01)

(58) Field of Classification Search
USPC ......................................................... 351/206
See application file for complete search history.

(56) References Cited

U.S. PATENT DOCUMENTS

2008/0225226 A1    9/2008  Fujishiro et al.

FOREIGN PATENT DOCUMENTS

JP          2008-228781         10/2008

*Primary Examiner* — Jack Dinh
(74) *Attorney, Agent, or Firm* — Rankin, Hill & Clark LLP

(57) ABSTRACT

A scanning laser ophthalmoscope includes: an irradiation optical system including a laser light source and an optical scanner; a light receiving optical system including first to third photo detectors; and a processor. The light receiving optical system includes a wavelength separator causing the light of a first wavelength range to be received by the first photo detector, the light of a second wavelength range to be received by the second photo detector, and the light of a third wavelength range to be received by the third photo detector. The processor generates a first fundus image on the basis of the light reception signal from the first photo detector, a second fundus image on the basis of the light reception signal from the second photo detector, and a third fundus image on the basis of the light reception signal from the third photo detector.

13 Claims, 11 Drawing Sheets

FIG. 2

|  | WAVELENGTH COMPONENT | EXEMPLARY USES |
|---|---|---|
| PHOTO DETECTOR 24 | RED | COLOR PHOTOGRAPHY |
|  | INFRARED (ICG FLUORESCENCE INFRARED COMPONENT) | ICG ANGIOGRAPHY |
| PHOTO DETECTOR 26 | GREEN | COLOR PHOTOGRAPHY, FAG ANGIOGRAPHY |
| PHOTO DETECTOR 28 | BLUE | COLOR PHOTOGRAPHY |
|  | NEAR-INFRARED | INFRARED PHOTOGRAPHY |

INFRARED PHOTOGRAPHY

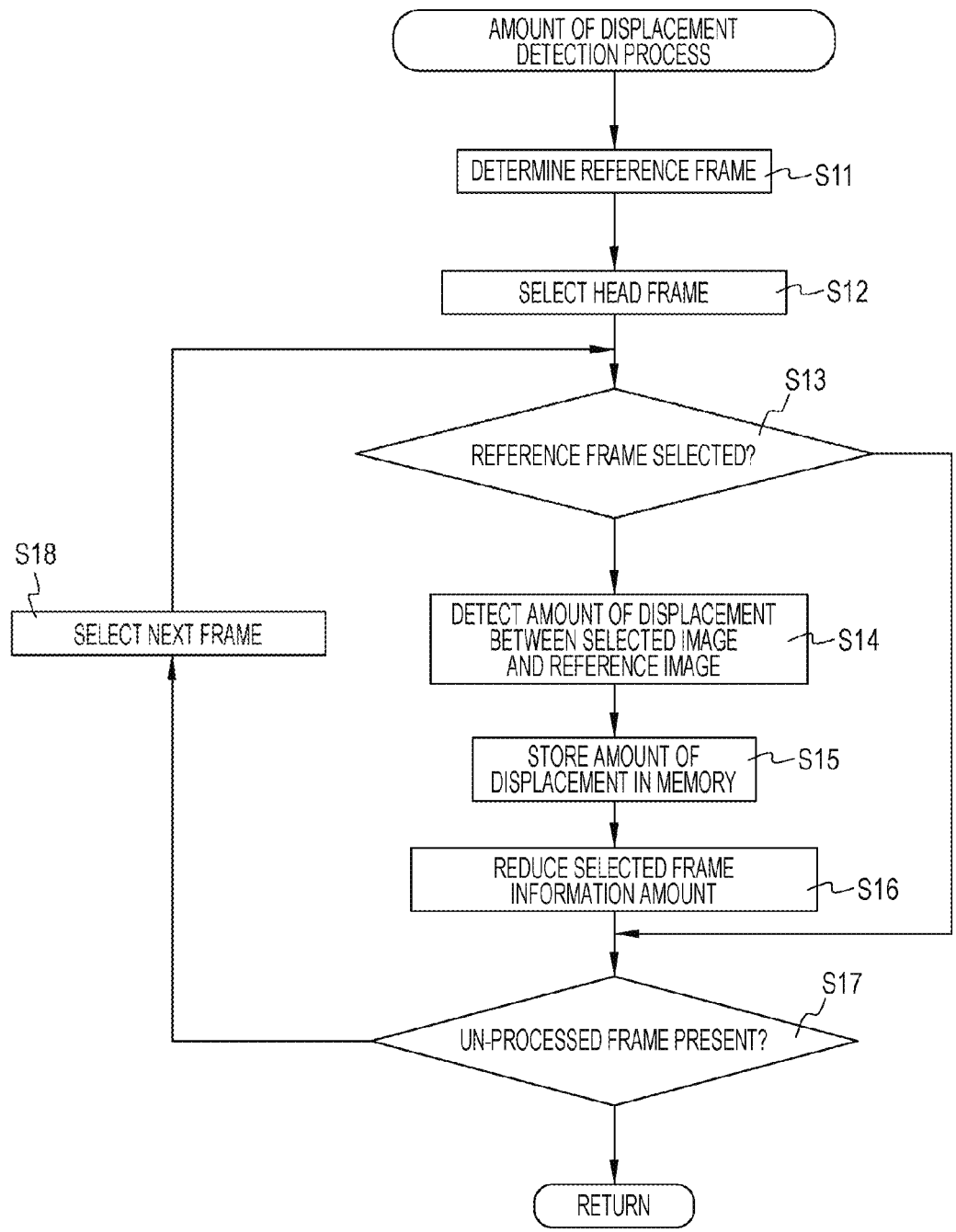

FIG. 11

| | WAVELENGTH COMPONENT | EXEMPLARY USES |
|---|---|---|
| PHOTO DETECTOR 24 | BLUE | COLOR PHOTOGRAPHY |
| | INFRARED (ICG FLUORESCENCE INFRARED COMPONENT) | ICG ANGIOGRAPHY |
| PHOTO DETECTOR 26 | RED | COLOR PHOTOGRAPHY |
| | NEAR-INFRARED | INFRARED PHOTOGRAPHY |
| PHOTO DETECTOR 28 | GREEN | COLOR PHOTOGRAPHY, FAG ANGIOGRAPHY |

FIG. 12

| | WAVELENGTH COMPONENT | EXEMPLARY USES |
|---|---|---|
| PHOTO DETECTOR 24 | BLUE | COLOR PHOTOGRAPHY |
| | NEAR-INFRARED | INFRARED PHOTOGRAPHY |
| PHOTO DETECTOR 26 | GREEN | COLOR PHOTOGRAPHY, FAG ANGIOGRAPHY |
| PHOTO DETECTOR 28 | RED | COLOR PHOTOGRAPHY |
| | INFRARED (ICG FLUORESCENCE INFRARED COMPONENT) | ICG ANGIOGRAPHY |

SCANNING LASER OPHTHALMOSCOPE

CROSS-REFERENCE TO RELATED APPLICATION

This application claims priority from Japanese Patent Application No. 2014-186906 filed with the Japan Patent Office on Sep. 12, 2014, the entire content of which is hereby incorporated by reference.

BACKGROUND

1. Technical Field

The present disclosure relates to a scanning laser ophthalmoscope for capturing a front image of an examinee's eye.

2. Description of the Related Art

A known scanning laser ophthalmoscope obtains a fundus image by scanning the fundus of the examinee's eye with laser light two-dimensionally. With regard to such technology, an apparatus has been proposed that performs a plurality of types of photography, such as infrared photography and fluorescence photography, by the single apparatus.

A technology of the relevant field is disclosed in JP-A-2008-228781, for example.

SUMMARY

A scanning laser ophthalmoscope includes: an irradiation optical system including a laser light source that outputs laser light and an optical scanner for two-dimensionally scanning fundus of an examinee's eye with the laser light; a light receiving optical system including first to third photo detectors that receive light obtained from the fundus as a result of the laser light irradiation of the fundus by the irradiation optical system; and a processor that generates a fundus image on the basis of a light reception signal from the photo detectors. The light receiving optical system includes a wavelength separator disposed in an optical path of the light receiving optical system so as to branch an optical path of the light obtained from the fundus into three branches and cause the light of a first wavelength range to be received by the first photo detector, the light of a second wavelength range different from the first wavelength range to be received by the second photo detector, and the light of a third wavelength range different from the first wavelength range and the second wavelength range to be received by the third photo detector. The processor generates a first fundus image on the basis of the light reception signal from the first photo detector, a second fundus image on the basis of the light reception signal from the second photo detector, and a third fundus image on the basis of the light reception signal from the third photo detector.

BRIEF DESCRIPTION OF THE DRAWINGS

FIG. 2 is a table showing the wavelength regions of light received by three photo detectors, and exemplary uses of the light of the respective wavelength regions.

FIG. 9 is a flowchart of an apparatus operation of during a displacement detection process.

FIG. 11 is a table showing the wavelength ranges of light received by photo detectors according to a first modification.

FIG. 12 is a table showing the wavelength ranges of light received by photo detectors according to a second modification.

DESCRIPTION OF THE EMBODIMENTS

Figure 1:
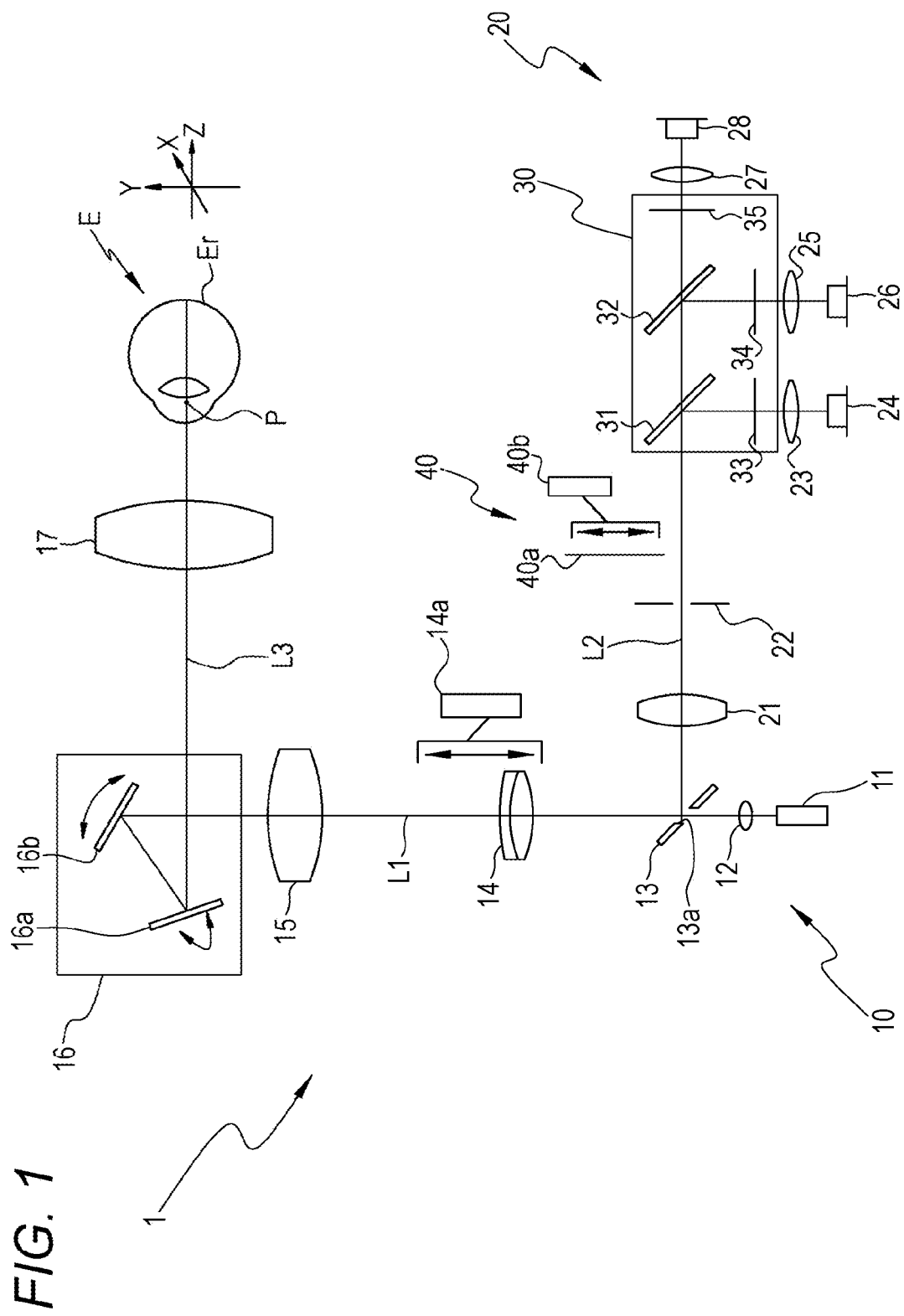
FIG. 1 is a schematic configuration diagram of an optical system provided in a scanning laser ophthalmoscope according to the present embodiment.

In the following detailed description, for purpose of explanation, numerous specific details are set forth in order to provide a thorough understanding of the disclosed embodiments. It will be apparent, however, that one or more embodiments may be practiced without these specific details. In other instances, well-known structures and devices are schematically shown in order to simplify the drawing.

When the fundus image is captured using a plurality of photographing techniques, the time required for the photographing tends to become longer, for example. As a result, the examiner and the examinee may feel burdened. In addition, the resolution of the fundus image may become decreased.

The present disclosure addresses the problem of providing a scanning laser ophthalmoscope capable of acquiring a plurality of fundus images in a preferable manner.

A scanning laser ophthalmoscope includes: an irradiation optical system including a laser light source that outputs laser light and an optical scanner for two-dimensionally scanning fundus of an examinee's eye with the laser light; a light receiving optical system including first to third photo detectors that receive light obtained from the fundus as a result of the laser light irradiation of the fundus by the irradiation optical system; and a processor that generates a fundus image on the basis of a light reception signal from the photo detectors. The light receiving optical system includes a wavelength separator disposed in an optical path of the light receiving optical system so as to branch an optical path of the light obtained from the fundus into three branches and cause the light of a first wavelength range to be received by the first photo detector, the light of a second wavelength range different from the first wavelength range to be received by the second photo detector, and the light of a third wavelength range different from the first wavelength range and the second wavelength range to be received by the third photo detector. The processor generates a first fundus image on the basis of the light reception signal from the first photo detector, a second fundus image on the basis of the light reception signal from the second photo detector, and a third fundus image on the basis of the light reception signal from the third photo detector.

According to the scanning laser ophthalmoscope, the fundus image can be acquired in a preferable manner using a plurality of light receiving conditions.

In the following, a typical embodiment will be described with reference to the drawings. FIG. 1 illustrates an optical system of a scanning laser ophthalmoscope (hereafter referred to as "SLO") 1 according to the present embodiment. The SLO 1 may be integrated with another ophthalmic apparatus, such as optical coherence tomography (OCT:) or a campimeter. The SLO 1 scans the fundus with laser light. The SLO 1 also captures a fundus image on the basis of light obtained from the fundus as a result of laser light irradiation. The SLO 1 according to the present embodiment can capture the fundus image on the basis of the fundus reflected light. In addition, the SLO 1 can capture the fundus image on the basis of fluorescence emitted from fluorescent material in the fundus.

<Configuration of Optical System>

With reference to FIG. 1, an optical system of the SLO 1 of the present embodiment will be described. According to the present embodiment, the SLO 1 includes an irradiation optical system 10 and a light receiving optical system 20 in a photographing unit, for example. The irradiation optical system 10 and the light receiving optical system 20 can capture a fundus front image on the basis of light under different photographing conditions (as will be described in detail later). In the following, a case will be described in which photographing light receiving conditions are varied as the photographing conditions. The irradiation optical system 10 irradiates the fundus Er of an examinee's eye E with laser light (illuminating light). According to the present embodiment, the irradiation optical system 10 includes a laser light source 11, a condenser lens 12, an apertured mirror 13, a lens 14, a lens 15, a scanning unit (optical scanner) 16, and an objective lens 17.

The laser light source 11 is a light source of the irradiation optical system 10. As the laser light source 11, a light source that outputs laser light (such as a laser diode (LD) or a super luminescent diode (SLD)) may be used. The laser light source 11 of the present embodiment is configured to output light of a plurality of wavelength ranges simultaneously. In other words, the laser light source 11 can generate synthetic light of a plurality of wavelength ranges. In this case, the laser light source 11 may include a plurality of light sources for the different wavelength ranges. For example, the laser light source 11 of the present embodiment outputs light of a total of four colors including three colors of blue, green, and red in the visible range, and one color in the infrared range. The three colors of blue, green, and red in the visible range are utilized for color photographing, for example. In the present embodiment, color photographing is performed using the fundus reflected light of the three colors of blue, green, and red. Of the three colors of the visible range, any one color may be utilized for visible fluorescence photography. For example, blue light may be utilized for FAG angiography (fluorescein angiography), which is a type of visible fluorescence photography. The light of the infrared range may also be utilized for infrared fluorescence photography as well as for infrared photography using the fundus reflected light of the infrared range. For example, as infrared fluorescence photography, ICG angiography (indocyanine green angiography) is known. In this case, the infrared light outputted from the laser light source 11 is preferably set to a wavelength range different from the fluorescence wavelength of the indocyanine green used for ICG angiography.

The laser light is guided from the laser light source 11 to the fundus Er along a path indicated by solid lines in FIG. 1. Specifically, the outputted laser light passes through the condenser lens 12 and then an opening portion 13a formed in the apertured mirror 13. Thereafter, the laser light passes through the lens 14 and the lens 15 and travels toward the scanning unit 16. The laser light that has passed through the scanning unit 16 passes through the objective lens 17 and then irradiates the fundus Er of the examinee's eye E. As a result, the light obtained from the fundus Er (i.e., reflected light, fluorescence and the like) is output from the pupil.

In the present embodiment, the lens 14 can be moved by a drive mechanism (actuator) 14a along an optical axis L1. In accordance with the position of the lens 14, the diopter scale of the irradiation optical system 10 and the light receiving optical system 20 is varied. In the present embodiment, by adjusting the position of the lens 14, an error of the diopter scale of the examinee's eye E is corrected (decreased). As a result, the position at which laser light is condensed can be adjusted to the location for observing the fundus Er (for example, the retinal surface).

The scanning unit (laser light scanning member) 16 is a unit for changing (deflecting) the direction of travel of laser light so as to scan the fundus with the laser light. In the present embodiment, the scanning unit 16 includes a resonant scanner 16a and a galvanometer mirror 16b. In the present embodiment, the resonant scanner 16a performs a laser light main-scan in the X-direction. The galvanometer mirror 16b performs a laser light sub-scan in the Y-direction. As the scanning unit 16, a reflective mirror (such as a galvanometer mirror, a polygon mirror, or a resonant scanner), or an acousto-optic modulator (AOM) for changing the direction of travel (deflection) of light may be used.

The objective lens 17 forms a pivot point P, which is the center of pivoting of the laser light that has passed through the scanning unit 16. In the present embodiment, the pivot point P is formed on an optical axis L3 of the objective lens 17 at a position optically conjugate with the scanning unit 16 (such as the mid-point of the resonant scanner 16a and the galvanometer mirror 16b) with respect to the objective lens 17. After passing through the scanning unit 16, the laser light passes through the objective lens 17 and is thereby irradiated onto the fundus Er via the pivot point P. Accordingly, the laser light that has passed through the objective lens 17 pivots about the pivot point P in accordance with the operation of the scanning unit 16. As a result, the fundus Er is scanned by the laser light two-dimensionally.

While in FIG. 1, the objective lens 17 is illustrated as a single objective lens, this is for the sake of convenience and does not suggest a limitation. The objective lens 17 may be configured from a plurality of lenses. As the objective lens 17, there may also be used a cemented lens comprising a plurality of lenses joined together, or an aspherical lens and the like.

The light receiving optical system 20 will be described. The light receiving optical system 20 includes a photo detector that receives the light obtained from the fundus Er as a result of laser light irradiation. The light receiving optical system according to the present embodiment has a structure enabling the reception of light with mutually different light receiving conditions (an example of photographing condition). In the present embodiment, between one light receiving condition and a light receiving condition different from that light receiving condition, at least one (at least some) of the wavelength ranges of the light received for capturing the fundus front image is different.

In the present embodiment, the light receiving optical system 20 includes three photo detectors 24, 26, and 28. The photo detectors 24, 26, and 28 may have sensitivity in different wavelength ranges. At least two of the photo detectors 24, 26, and 28 may have sensitivity in a common wavelength range. As the photo detectors 24, 26, and 28, avalanche photodiodes (APD) may be used. The photo detectors 24, 26, and 28 respectively output a signal corresponding to the strength of the received light (hereafter referred to as a light reception signal). In the present embodiment, the light reception signal is processed separately for each photo detector so as to generate an image. Namely, in the present embodiment, a maximum of three types of fundus images are generated in parallel.

The light receiving optical system 20 of the present embodiment also includes a light separation unit 30 for separating the light obtained from the fundus Er. The wavelength separator, disposed in the optical path of the light receiving optical system 20, may include a light separation unit 30 with a structure disposed the optical path of the light receiving optical system 20, as illustrated in FIG. 1. In the present embodiment, the light separation unit 30 includes dichroic mirrors 31 and 32 and filters 33, 34, and 35.

The light separation unit 30 of the present embodiment divides the optical path of the light receiving optical system 20 into three branches. The light separation unit 30 also separates the wavelengths of the light obtained from the fundus Er. As will be described in detail below, in the present embodiment, the optical path is branched by the two dichroic mirrors (dichroic filters) 31 and 32. At the end of each of the branch optical paths, one of the photo detectors 24, 26, and 28 is disposed.

As will be described in detail below, the light separation unit 30 separates the wavelengths of the light obtained from the fundus Er, and causes the three photo detectors 24, 26, and 28 to receive light of mutually different wavelength ranges. Namely, the photo detector 24, the photo detector 26, and the photo detector 28 respectively receive light of a first wavelength range, light of a second wavelength range, and light of a third wavelength range separately. For the light of the first wavelength range, the light of the second wavelength range, and the light of the third wavelength range, any of the fundus reflected light of the blue wavelength range, the fundus reflected light of the green wavelength range, and the fundus reflected light of the red wavelength range may be separately allocated, for example. Alternatively, for the light of the first wavelength range, the light of the second wavelength range, and the light of the third wavelength range, any of the fundus reflected light of the infrared range wavelength range, fluorescence of the first wavelength range, and fluorescence of the second wavelength range may be separately allocated. Herein, the light separation unit 30 causes each of the photo detectors 24, 26, and 28 to receive the light of one of the three colors of blue, green, and red. The light separation unit 30 also guides the fluorescence obtained from the fundus during fluorescence photography and the fundus reflected light of the infrared range used for infrared photography to respectively different photo detectors. In this case, the light separation unit 30 of the present embodiment guides the fluorescence obtained from the fundus by infrared fluorescence photography and the fluorescence obtained from the fundus by visible fluorescence photography to respectively different photo detectors. Further, the light separation unit 30 of the present embodiment guides the light of a wavelength range for excitation light during fluorescence photography and fluorescence based on the excitation light to respectively different photo detectors. In the present embodiment, the dichroic mirrors 31 and 32 perform rough wavelength separation. The filters 33, 34, and 35 are used, for example, for removing (separating from the fundus fluorescence) the fundus reflected light of the excitation light when fluorescence photography is performed.

In the present embodiment, the light receiving optical system 20 also includes a lens 21, a pinhole plate 22, and lenses 23, 25, and 37. Further, the light receiving optical system 20 of the present embodiment includes a filter inserting/removing unit 40.

The pinhole plate 22 is disposed at a position conjugate with the fundus Er, and is utilized as a confocal diaphragm. The light receiving optical system 20 shares the members disposed between the objective lens 17 and the apertured mirror 13 with the irradiation optical system 10. As a result, in the present embodiment, the optical path from the examinee's eye E to the apertured mirror 13 is formed as a common portion of the irradiation optical system 10 and the light receiving optical system 20.

The light from the fundus Er travels backward along the irradiation optical system 10 and irradiates the apertured mirror 13. By being reflected by the apertured mirror 13, the light is guided to the lens 21. The light that has passed through the lens 21 is focused at an opening 22a of the pinhole plate 22. The light that has passed through the opening 22a is guided to the dichroic mirror 31. The dichroic mirror 31 and the dichroic mirror 32 reflect light of specific wavelength ranges and transmit light of the other wavelength ranges. In the present embodiment, the reflected wavelength range and the transmitted wavelength range are different between the mirrors. Thus, to each of the branched optical paths, light of a different wavelength range from the other optical path is guided.

To the optical path on the photo detector 24 side, the light of the wavelength range reflected by the dichroic mirror 31 is guided. The dichroic mirror 31 reflects at least the light of the red wavelength range and the light of the infrared range (first infrared range), while transmitting the light of the other wavelength ranges. Thereafter, some of the wavelength ranges are further removed by the filter 33. The light that has passed through the filter 33 is received by the photo detector 24 via the lens 23. As a result, as illustrated in FIG. 2, the photo detector 24 receives the light of the red wavelength range and the light of the infrared range (first infrared range). The red wavelength range is utilized for color photographing, for example. The first infrared range is utilized for ICG angiography, for example. Namely, in the present embodiment, the first infrared range is set so as to include the infrared component comprising the fluorescence wavelength of indocyanine green.

To the optical path on the photo detector 26 side, the light of the wavelength range that has passed through the dichroic mirror 31 and that has been reflected by the dichroic mirror 32 is guided. In the present embodiment, the dichroic mirror 32 reflects at least the light of the green wavelength range. Of the reflected light, the light of the wavelength range that has passed through the filter 34 is received by the photo detector 26 via the lens 25. As a result, as illustrated in FIG. 2, the photo detector 26 receives the light of the green wavelength range. The green wavelength range is utilized for color photographing, and also for FAG angiography in the present embodiment. Namely, in the present embodiment, the green wavelength range is set so as to include the green component comprising the fluorescence wavelength of fluorescein.

To the optical path on the photo detector 28 side, the light of the wavelength range that has passed through the two dichroic mirrors 31 and 32 is guided. In the present embodiment, at least the light of the blue wavelength range and the light of the infrared range are transmitted. The infrared light that passes through the dichroic mirrors 31 and 32 has a wavelength range on the shorter wavelength side than the infrared light reflected by the dichroic mirror 31. Of the light that has passed through the dichroic mirrors 31 and 32, the light of the wavelength range that has passed through the filter 35 is received by the photo detector 28 via the lens 27. As illustrated in FIG. 2, as a result, the photo detector 28 receives the light of the blue wavelength range and the light of a second infrared range on the shorter wavelength side than the first infrared range. The blue wavelength range is utilized for color photographing, for example. The second infrared range is utilized for infrared photography, for example.

The filter inserting/removing unit 40 is a mechanism for inserting or removing the filter for removing the fundus reflected light of the excitation light during fluorescence photography from the optical path. In the present embodiment, the filter inserting/removing unit 40 includes a filter 40a and a drive mechanism (actuator) 40b. For example, the filter 40a is inserted in the optical path when FAG angiography is performed. In this case, the filter 40a blocks light of the blue wavelength range, that is the fundus reflected light of the excitation light. The filter 40a of the present embodiment transmits light of wavelength ranges other than the blocked wavelength range. Thus, in addition to the green fluorescence generated from the fluorescein, the fundus reflected light in the infrared range also passes through the filter 40a. When FAG angiography is not performed, the filter 40a is withdrawn from the optical path. The drive mechanism 40b of the present embodiment is configured to move the filter 40a in a direction intersecting the optical axis of the light receiving optical system 20 so as to insert or remove the filter 40a. The inserting/removing technique, however, is not necessarily limited to the above.

<Configuration of Control System>

Figure 3:
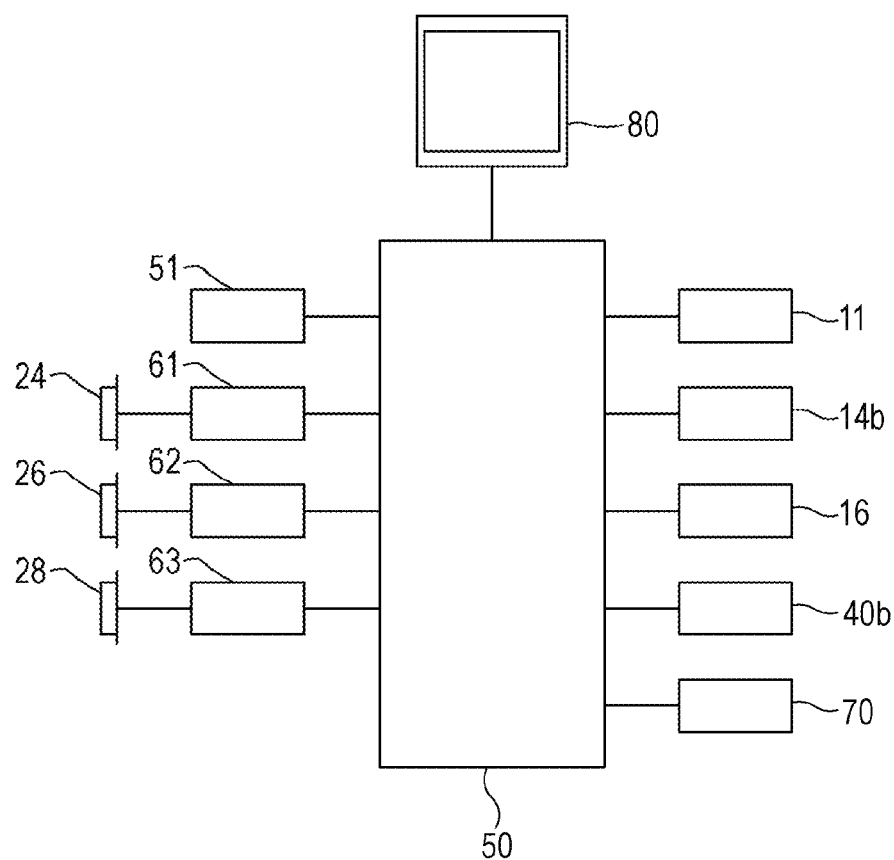
FIG. 3 is a schematic configuration diagram of a control system provided in the scanning laser ophthalmoscope according to the present embodiment.

With reference to FIG. 3, the control system of the SLO 1 will be described. In the SLO 1, various units are controlled by a control unit 50. The control unit 50 is a processing device (processor) including an electronic circuit. The control unit 50 performs a control process for the various units of the SLO 1 and a calculation process. The control unit 50 includes a central processing unit (CPU) and memory and the like, for example. The control unit 50 is electrically connected to a storage unit 51 and each of image generating units (processors for image processing) 61, 62, and 63 via a bus and the like. The control unit 50 is also electrically connected to the laser light source 11, the drive mechanism 14a, the scanning unit 16, the drive mechanism 40b, an operating unit 70, and a display 80 and the like.

In the storage unit 51, various control programs and fixed data and the like are stored. In the storage unit 51, images captured by the SLO 1 and temporary data and the like may also be stored.

The image generating units 61, 62, and 63 are processing devices for generating a fundus image on the basis of the light reception signals output from the photo detectors 24, 26, and 28. The image generating units 61, 62, and 63 may be independent from the control unit 50. Alternatively, the control unit 50 may include the image generating units 61, 62, and 63. In the following description, the image generating units 61, 62, and 63 are assumed to be devices (such as ICs or LSIs) independent from the control unit 50.

As illustrated in FIG. 3, the image generating unit 61 is connected to the photo detector 24, the image generating unit 62 is connected to the photo detector 26, and the image generating unit 63 is connected to the photo detector 28. For example, the image generating unit 61 constructs (generates) one frame of fundus image each time it receives the light reception signal for one frame from the photo detector 24. Similarly, in the image generating unit 62 and the image generating unit 63, fundus images are successively generated on the basis of the light reception signal from the respectively connected photo detectors. In the present embodiment, the control unit 50 controls the timing of generation of the fundus image by the image generating units 61, 62, and 63 (namely, the timing of generation of the image in the SLO 1). In the present embodiment, the control unit 50 synchronizes the timing of generation of the images in the image generating units 61, 62, and 63.

In the present embodiment, the control unit 50 further performs an image process using the images generated by the image generating units 61, 62, and 63. For example, the control unit 50, when the three colors of visible light are output from the laser light source 11, combines the images generated by the image generating units 61, 62, and 63 so as to generate a color image. Examples of other processes will be described below.

The control unit 50 controls the various members described above on the basis of an operation signal output from the operating unit 70. To the operating unit 70, a mouse and keyboard and the like are connected as operating members operated by the examiner.

<Operation of Apparatus>

The operation of the SLO 1 having the above-described configuration will be described with reference to a flowchart of FIG. 4. In the SLO 1, when the power supply is switched on, a main process is executed by the control unit 50 in accordance with a control program stored in the storage unit 51. The SLO 1 is operated according to the main process.

Figure 4:
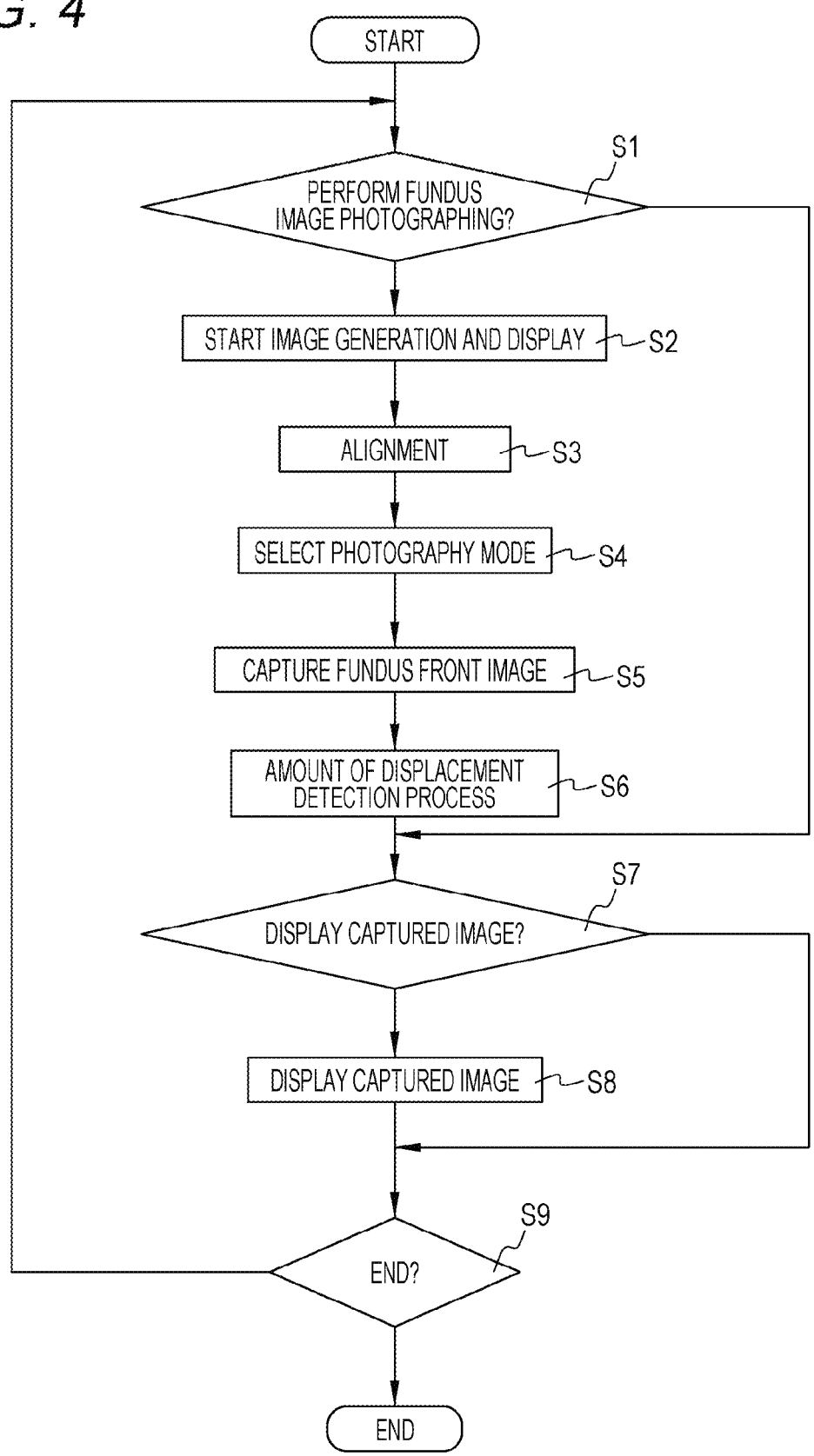
FIG. 4 is a flowchart of an operation of an apparatus in a main process.

In the example of FIG. 4, the main process largely includes a process regarding the capturing of the fundus image, and a process regarding the displaying of a previously captured image. In this case, in the main process, it may be initially determined whether a photographing operation or a captured image display operation is to be performed (S1, S7). For example, the determination may be made on the basis of an instruction input from the outside via the operating unit 70. The photographing operation and the captured image display operation may be switched as needed at the timing at which the instruction is input from the outside, and is not limited only to the timing at which the photographing operation or the display operation is not started (or is completed).

<Photography Procedure>

The case where the capturing of the fundus image is performed (S1: Yes) will be described.

First, fundus image generation and the displaying of the generated image are started (S2). For example, the control unit 50 causes the laser light source 11 to output light. The control unit 50 also causes the display 80 to display the images successively generated by at least one of the image generating units 61, 62, and 63. As a result, a live image of the examinee's eye E is displayed on the display 80. In this case, the control unit 50 causes the display 80 to display a live infrared image, for example.

Then, the apparatus body of the SLO 1 is aligned with the examinee's eye E (S3). The alignment involves, for example, adjusting the relative positions of the examinee's eye E and the apparatus body on the basis of alignment information (such as image information of the examinee's eye). For example, when the apparatus body of the SLO 1 is configured so as to be moved by the operation of a joystick, which is not shown, the examiner can make the alignment manually by operating the joystick while monitoring an image of the examinee's eye E being displayed on the display 80. At this time, the examiner instructs the examinee to gaze a fixation target, not shown. As a result of the adjustment of the positional relationship between the apparatus body and the examinee's eye E in the X-, Y-, and Z-directions, a fundus image is displayed on the display 80.

A diopter scale correction may also be performed. As described above, the diopter scale correction is made by adjusting the position of the lens 14. For example, the examiner manually makes the diopter scale correction while monitoring the fundus image displayed on the display 80. In this case, the control unit 50 adjusts the lens 14 position by driving the drive mechanism 14*a* on the basis of an operation signal from the operating unit 70. The examiner adjusts the position of the lens 14 so that a clearer fundus image can be displayed.

<Mode Setting>

Then, in the present embodiment, in accordance with the type of image for the examiner to perform fundus observation and photographing, the mode of the SLO 1 (photographing mode) is set (S4). For example, according to the present embodiment, the photographing mode includes a normal photographing mode, a color photographing mode, an infrared fluorescence photographing mode, a visible fluorescence photographing mode, a simultaneous fluorescence photographing mode, and an FAF angiography mode. The photographing mode may be selected on the basis of an instruction from the examiner via the operating unit 70.

The normal photographing mode and the color photographing mode are selected when observation and photography are implemented using the fundus image generated on the basis of the fundus reflected light. In the normal photographing mode, as the image for observation and as the captured image, the fundus image based on the fundus reflected light of the infrared range (i.e., an infrared image) is generated and displayed. The light of the infrared range does not readily cause miosis of the examinee's eye E and is therefore suitable for observation. The infrared image has superior contrast and is therefore suitable for discovering a lesioned part from the fundus as a whole. The infrared photographing mode may be the reference mode (set by default) of the SLO 1.

The color photographing mode is selected when observation and photography are implemented using the color fundus image generated on the basis of the fundus reflected light of the three colors of blue, green, and red. In the color photographing mode of the present embodiment, as the image for observation, the fundus image based on the fundus reflected light of the infrared range (i.e., an infrared image) is generated and displayed. In the present embodiment, as the captured image, a color image is generated. The color image is suitable for discovering a lesioned part based on color information.

Figure 5:
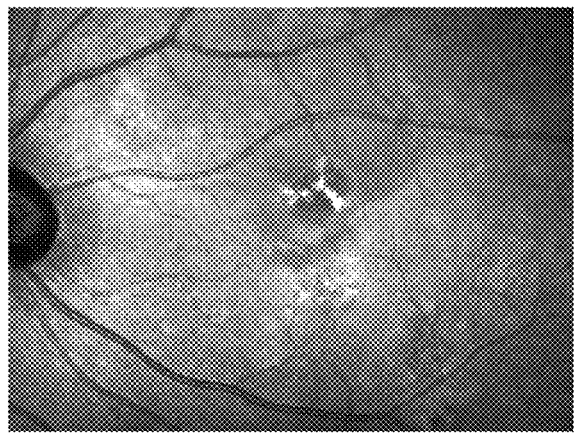
FIG. 5 shows an infrared image captured by infrared photography.

In this mode, during observation, light of the infrared range is output from the laser light source 11. In this case, an infrared image is generated by the image generating unit 63 (see FIG. 5).

Further, during the photographing, the control unit 50 causes the laser light source 11 to output light of the three colors of blue, green, and red. In the present embodiment, the three colors of light are simultaneously output. In this case, the image generating unit 61 generates a fundus image based on the red fundus reflected light. The image generating unit 62 generates a fundus image based on the green fundus reflected light. The image generating unit 63 generates a fundus image based on the blue fundus reflected light. The control unit 50 combines the three types of images generated by the three image generating units 61, 62, and 63 into one, obtaining a color fundus image.

The infrared fluorescence photographing mode is selected when the infrared fluorescence image is observed and captured. In the present embodiment, ICG angiography is performed in the infrared fluorescence photographing mode, for example. In this mode, the control unit 50 causes the laser light source 11 to output infrared light. As a result, the image generating unit 61 generates a fundus image based on the fluorescence of indocyanine green as the contrast agent (see FIG. 6). Further, in the present embodiment, an infrared image is generated by the image generating unit 63 on the basis of the fundus reflected light. Namely, the control unit 50 causes the image generating unit 61 to generate the infrared fluorescence image and also causes the image generating unit 63 to generate the infrared image.

The visible fluorescence photographing mode is selected when the visible fluorescence image is observed and captured. In the present embodiment, in the visible fluorescence photographing mode, FAG angiography is performed, for example. In this mode, the control unit 50 causes the laser light source 11 to output not only the blue light used as the excitation light for the fluorescein that is the contrast agent, but also infrared light. The control unit 50 also controls the filter inserting/removing unit 40 to insert the filter 40*a* in the optical path of the light receiving optical system 20. Thus, the blue fundus reflected light being guided toward the photo detector 28 is blocked. As a result, the image generating unit 62 generates a fundus image based on the fluorescence of the fluorescein that is the contrast agent (see FIG. 6). The image generating unit 63 generates an infrared image based on the fundus reflected light.

The simultaneous fluorescence photographing mode is selected when two types of fluorescence images are simultaneously captured. In the present embodiment, for example, infrared fluorescence photography and visible fluorescence photography (more specifically, ICG angiography and FAG angiography) are simultaneously performed. By having the laser light source 11 output infrared light and blue light, fluorescence is generated by the indocyanine green and the fluorescein administered to a blood vessel. Thus, the control of the laser light source 11 and the filter inserting/removing unit 40 by the control unit 50 is based on the visible fluorescence photographing mode. Meanwhile, in the simultaneous fluorescence photographing mode, the control unit 50 causes each of the three image generating units 61, 62, and 63 to generate an image. Namely, an infrared fluorescence image, a visible fluorescence image, and an infrared image are respectively generated by the image generating units 61, 62, and 63. In this case, the infrared fluorescence and the visible fluorescence may be received simultaneously, or there may be a slight time lag between the timings of generation of the respective images based on the light reception signals. Namely, in the present embodiment, when the respective images are simultaneously captured, there may be a time lag between the timing of image generation and the timing of image data formation by the control unit 50.

Figure 7A:
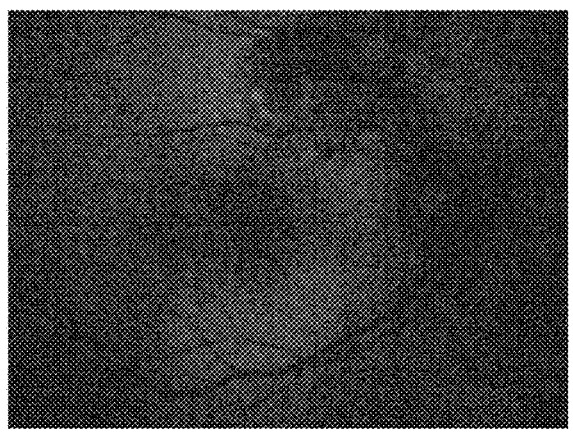
FIG. 7A shows an autofluorescence image captured by FAF angiography.
Figure 7B:
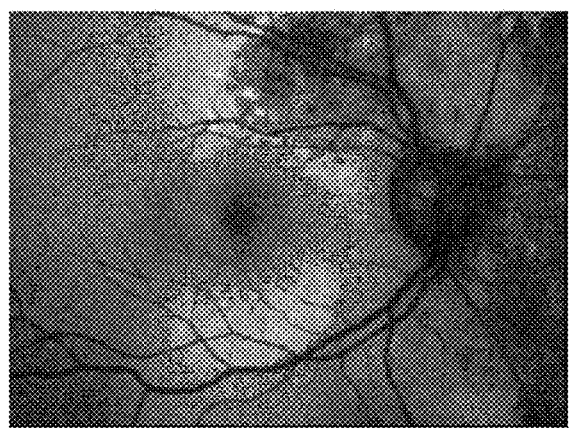
FIG. 7B shows an arithmetic mean image obtained from a plurality of autofluorescence images.

The FAF angiography mode is selected when an autofluorescence image is observed and captured. In the FAF angiography mode of the present embodiment, the autofluorescence image of lipofuscin accumulated in the fundus is observed and captured, for example. The autofluorescence image is useful for diagnosing age-related macular degeneration, for example. In this case, the control unit 50 of the present embodiment causes the laser light source 11 to output blue or green visible light and infrared light. The visible light is lipofuscin excitation light, and the infrared light is the light for capturing an infrared image. In the present embodiment, the image is generated using fluorescence on the longer wavelength side than the excitation light. Namely, when blue light is the excitation light, the image generated by the image generating unit 62 is an autofluorescence image (see FIG. 7A). When green light is the excitation light, the image generated by the image generating unit 61 is an autofluorescence image. Also, an infrared image is generated by the image generating unit 63.

By setting the photographing mode, the fundus image obtained in accordance with the light receiving condition corresponding to the mode is displayed on the display 80. In the present embodiment, a live image obtained in accordance with the light receiving condition is displayed. Thus, the examiner can observe the fundus using the live image corresponding to the mode.

Figure 8:
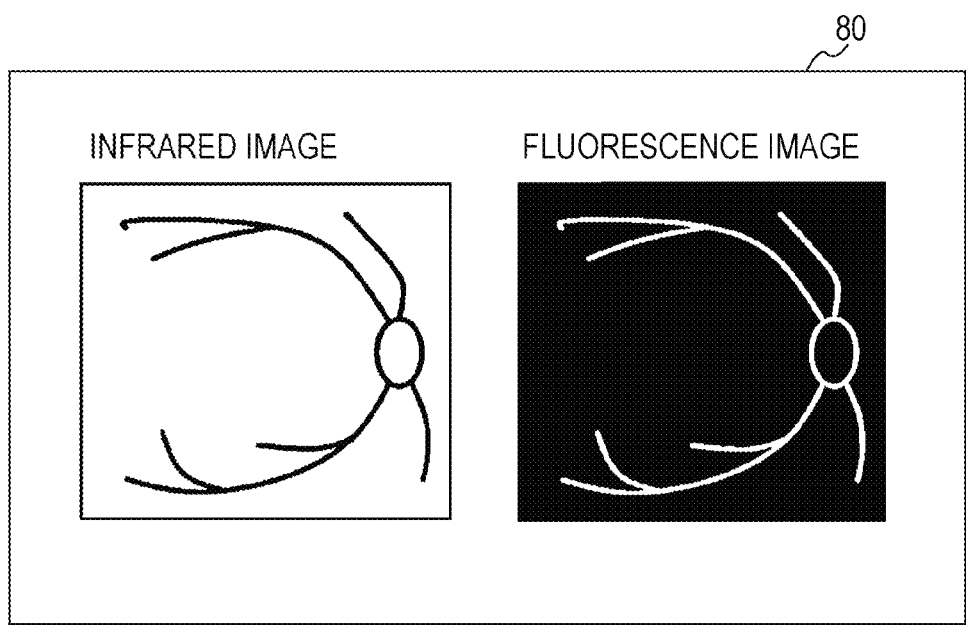
FIG. 8 illustrates an example of the manner of display of a fundus image on a display.

When any of the fluorescence photographing modes is set, in the present embodiment, an infrared image is obtained in addition to the fluorescence image (at least an infrared fluorescence image or a visible fluorescence image). In this case, the control unit (display control member) 50 causes the fluorescence image and the infrared image to be displayed on the display 80 side by side (see FIG. 8). In particular, in the case of the simultaneous fluorescence mode, the control unit 50 causes the visible fluorescence image, the infrared fluorescence image, and the infrared image to be displayed on the display 80 side by side. The infrared image and the fluorescence image are images of the same range of the fundus. Accordingly, by referencing the infrared image, the examiner can easily grasp a position on the fundus in the fluorescence image, for example.

<Capturing of the Fundus Image>

The capturing of the fundus image (S5) may be executed when, for example, a photographing start instruction is input by the examiner. In this case, photographing is performed when a photography signal is received by the control unit 50 from the operating unit 70. The photographing involves the control unit 50 storing images generated by the image generating units 61, 62, and 63 in the storage unit 51 as captured images. In the present embodiment, the image generating units 61, 62, and 63 used for photographing generate a plurality of temporally successive frames of images by a single photographing. In the following, the plurality of temporally successive frames of images generated by the single photographing will be referred to as a frame group. The number of images acquired by the single photographing, however, is not necessarily required to be more than one, and one frame of image may be acquired by the single photographing.

<Displacement Detection Process>

When the fundus image is captured, the control unit 50 performs a displacement detection process (S6). In the displacement detection process in S6, the amount of displacement of two or more fundus images captured at different timings is detected. The displacement detected by the SLO 1 (control unit 50) may include an image-to-image displacement with respect to the XY-directions and/or the rotation direction of the image, or distortion in each image and/or an image-to-image displacement with respect to the magnification ratio of each image. In the process of S6, the amount of displacement of each image included in one frame group is detected on the frame unit basis (namely, for each frame). In the present embodiment, the amount of displacement of each frame is detected as a relative value with respect to a reference frame. The reference frame may be one frame in the frame group for which the displacement detection is performed. The detected amount of displacement is utilized for correcting the displacement of images included in the frame group, for example.

In some of the photographing modes, as described above, the SLO 1 of the present embodiment performs photographing control to associate a second fundus front image when capturing a first fundus front image. The first fundus front image is a fundus image captured on the basis of the light under a first light receiving condition. The second fundus front image is a fundus image captured on the basis of a light receiving condition different from the first light receiving condition. For example, according to the present embodiment, the SLO 1 captures the first fundus front image and the second fundus front image in association with each other by capturing the images approximately simultaneously. In the present embodiment, as a result of the photographing control, two or more types of fundus images with different light receiving conditions are included in one frame group. In the displacement detection process (S6), a second displacement which is a displacement between the second fundus front images captured at different timings is the displacement between the first fundus front images respectively corresponding to the second fundus front images. The second displacement is detected on the basis of a first displacement calculated by an image process. As will be described in detail below, depending on the light receiving condition such as fluorescence photography, it may be difficult to detect a displacement from the captured image itself. In this regard, according to the present embodiment, the SLO 1, when capturing an image under one light receiving condition (such as fluorescence photography), captures a fundus image of a different light receiving condition (such as infrared photography) simultaneously. In this case, no displacement is caused between the images obtained simultaneously under the two light receiving conditions. Accordingly, using the amount of displacement between the first fundus front images, the amount of displacement in the fundus image obtained under the second light receiving condition can be easily and accurately obtained.

In the present embodiment, the light receiving optical system 20 is set to receive the fundus reflected light of laser light under the first light receiving condition, and to receive the fluorescence caused in the fundus Er using laser light as the excitation light under the light receiving condition different from the first light receiving condition. Namely, the first fundus front image is an image based on the fundus reflected light. The second fundus front image is a fluorescence image. As described above, in the present embodiment, when the fluorescence image is captured, an infrared image is captured in association. Thus, in the present embodiment, as the first fundus front image, an infrared reflect image is utilized. Accordingly, in the process of S6, when a fluorescence image and an infrared image are included in one frame group, the control unit 50 obtains the amount of displacement of each frame by determining the amount of displacement between the infrared reflect images. In this case, the amount of displacement of the infrared image of each frame is estimated as the amount of displacement of the fluorescence image of each frame.

Figure 6:
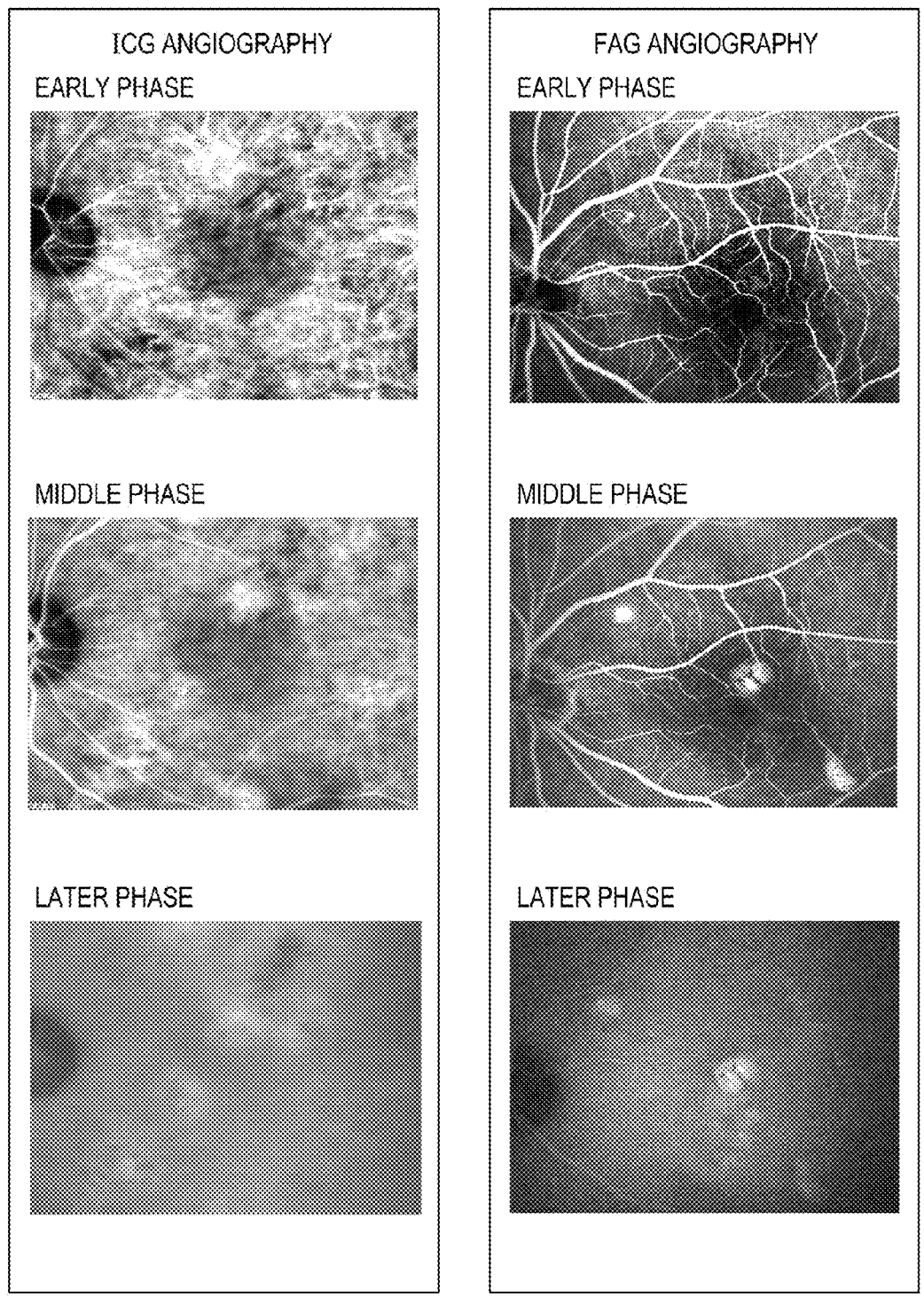
FIG. 6 shows infrared fluorescence images at different time phases captured by ICG angiography, and visible fluorescence images at different time phases captured by FAG angiography.

For example, in a contrast fluorescence image, the state of the image is greatly varied from one time phase to another by the inflow of contrast agent (see FIG. 6). Accordingly, it is difficult to detect the amount of displacement from the fluorescence image per se. Further, in an autofluorescence image, it is difficult to obtain an image with a high S/N ratio due to the small light amount of fluorescence (see FIG. 7A). Accordingly, detection of the amount of displacement from the autofluorescence image per se is difficult. On the other hand, an infrared reflect image tends to have a high S/N ratio. In addition, the infrared reflect image is not readily subject to the influence of the flow of contrast agent. Thus, when contrast fluorescence photography is performed, temporal changes do not readily occur in the infrared reflect image. Accordingly, in either case, the detection of the displacement between infrared reflect images can be easily and accurately performed. In the present embodiment, the amount of displacement between the infrared reflect images is also applied to a fluorescence image. Accordingly, the control unit 50 can acquire the amount of displacement of the fluorescence image in a preferable manner.

The control unit 50 may be configured to compress the data amount of the fundus front image to the extent enabling displacement detection, and then determine the displacement in a post-processing step. For example, the control unit 50 saves the fundus front image after filtering (such as phase information detection or image smoothing), and determines the displacement detection in a subsequent step.

With reference to the flowchart of FIG. 9, the details of the displacement detection process will be described.

Figure 10A:
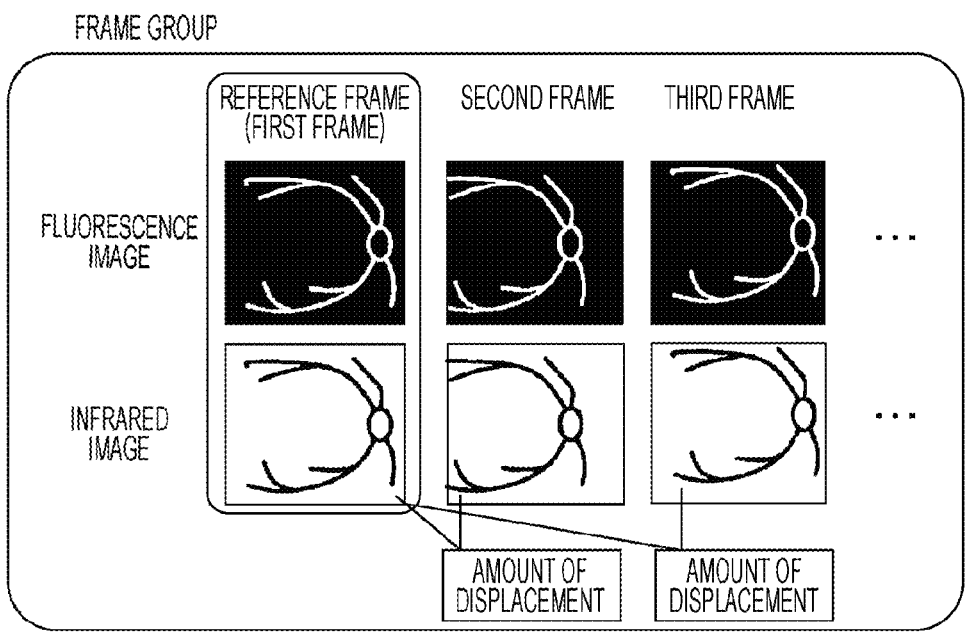
FIG. 10 schematically illustrates the outline of the displacement detection process.

First, the reference frame is determined (S11). The reference frame may be determined manually or automatically. In the case of manual determination, the control unit 50 displays a list of images included in a frame group. The control unit 50 then selects a reference frame from the list on the basis of an operation by the examiner received via the operating unit 70, for example. In the case of automatic determination, the reference frame may be determined on the basis of information obtained from each image, such as image quality information. The reference frame may be determined in advance. For example, one frame at the head of the frame group may be determined as the reference frame (see FIG. 10A).

Then, the control unit 50 selects the frames one by one, and detects the amount of displacement of the selected frames successively. First, the control unit 50 selects the head frame (S12).

Then, the control unit 50 determines whether the selected frame is the reference frame (S13).

If the selected frame is the reference frame, no displacement will be generated in the first place. Thus, if it is determined that the selected frame is the reference frame (13: Yes), the control unit 50 skips the process of S14 to S16 and transitions to the process of S17. In this case, the control unit 50 may store "zero" in the storage unit 51 as the amount of displacement of the reference frame, for example.

In the process of S13, if it is determined that the frame is not the reference frame (S13: No), the amount of displacement between the reference frame and the selected frame is detected (S14). For detecting the amount of displacement, various image processing techniques (such as a method using various correlation functions, a method using Fourier transform, and a method based on feature point matching) may be used.

For example, as a method of detecting the amount of displacement, a technique may involve causing a pixel-by-pixel displacement in a predetermined reference image (such as an infrared image of the reference frame) or an object image (an infrared image of the selected frame), comparing the reference image and the object image, and detecting the amount of displacement between the data when the data are matched the most (i.e., when the highest correlation is achieved). As a method of detecting the amount of displacement, a technique may involve extracting common feature points from the predetermined reference image and the object image, and detecting a displacement of the extracted feature points. In the present embodiment, the control unit 50 uses a technique including extracting common feature points from two infrared images, and detecting the amount of displacement of the extracted feature points.

When infrared images and fluorescence images are included in one frame group, the control unit 50 determines the amount of displacement of each frame by comparing the infrared images included in the frames, as described above (see FIG. 10A).

The control unit 50 stores the acquired amount of displacement in the storage unit 51 as the amount of displacement of the selected frame (S15).

Figure 10B:
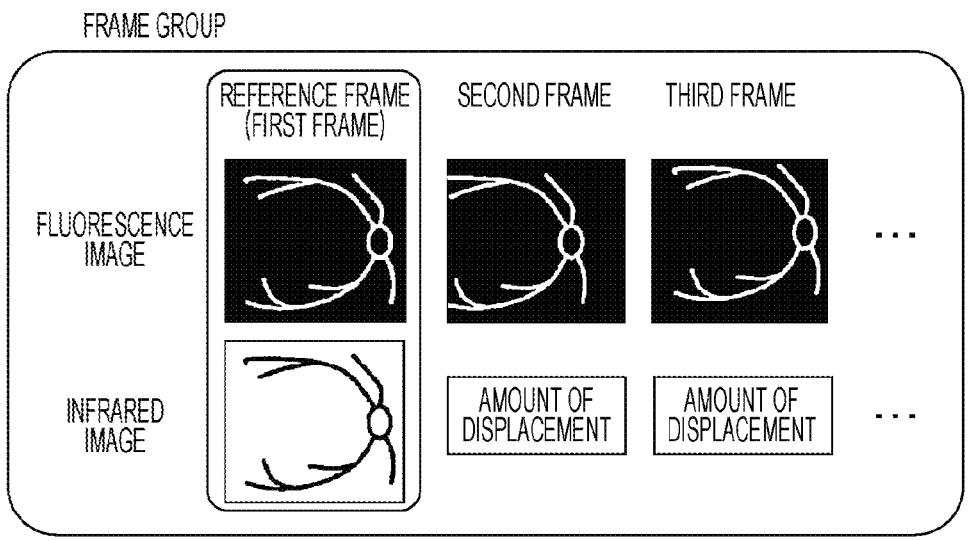

Thereafter, in the present embodiment, the amount of information of the selected frame is reduced (S16). In the present embodiment, the reduction of the amount of information is performed with respect to the frame group including fluorescence images and infrared images, for example. More specifically, the amount of information is reduced by deleting the infrared images included in the frame group. In this case, for example, the infrared images other than the infrared image of the reference frame may be deleted from the storage unit 51, leaving the infrared image of the reference frame, as illustrated in FIG. 10B. The remaining infrared image of the reference frame may be used for display together with the fluorescence image. Another technique for reducing the amount of information may include resizing (image compression) of the stored images. In this case, the infrared images stored in the storage unit 51 are replaced by resized images. The lower limit of the size of the image after resizing may be a minimum size such that image positioning between the resized images can be performed.

After S16, the control unit 50 determines whether there is a frame for which detection of the amount of displacement has not been performed (un-processed frame) (S17). If there is the un-processed frame (S17: Yes), the control unit 50 selects the next frame (S18). Thereafter, the control unit 50 returns to S13 and repeats the execution of the process of S13 to S18 until the amount of displacement is detected for all of the frames. If the amount of displacement has been detected for all of the frames (S17: No), the control unit 50 ends the displacement detection process.

As a result of the displacement detection process, the amount of displacement of each image included in the frame group is obtained on a frame by frame basis. Also, the amount of displacement on a frame by frame basis is stored in the storage unit 51. At this time, as described above, the infrared images included in the frame group are deleted, whereby the amount of information stored in the storage unit 51 is reduced. Accordingly, the storage capacity of the storage unit 51 can be effectively utilized.

<Display of Captured Image>

The case where the display of the previously captured image is performed (S7: Yes) will be described.

In the example of FIG. 4, captured image enlarging display is executed in the process of S8. For example, the control unit 50 causes the second fundus front images corrected on the basis of the first displacement to be displayed side by side on the display 80. The control unit 50, when displaying a marker for designating the same position on each of the second fundus front images arranged on the display 80, may correct the marker display position on the basis of the calculated first displacement.

In the following, an example will be described in which, when a plurality of frame groups are stored in the storage unit 51 in advance, display is performed on the basis of one of the frame groups. In the present embodiment, the control unit 50, in order to cause the examiner to select a captured image to be displayed as enlarged, displays a list of the frame groups stored in the storage unit 51. The control unit 50 then causes the fundus image to be displayed on the display 80 as enlarged on the basis of the frame group selected from the list by the examiner.

In this case, the control unit 50 of the present embodiment first corrects the displacement of each image included in the selected frame group. For the displacement correction, the amount of displacement of each frame that is stored in the storage unit 51 together with the flame group is used. For example, the control unit 50 corrects the displacement by moving the image of each frame other than the reference frame by the amount of displacement of each frame. After the displacement correction, the control unit 50 may subject a plurality of images that have been corrected to an arithmetic mean process, and cause a resultant arithmetic mean image to be displayed on the display 80. After the displacement correction, the control unit 50 may display the frames constituting the frame group continuously as a moving image. In the present embodiment, the images (which are infrared images in the present embodiment) deleted in the process of S16 for information amount reduction, leaving the reference frame, are not subjected to the displacement correction.

If two or more types of fundus images obtained under different light receiving conditions are included in the selected frame group, the control unit 50 may cause the fundus images (captured images) of the respective types to be displayed on the screen of the display 80 side by side. In this way, the examiner can grasp the state of the fundus on the basis of the different types of images in a preferable manner.

The SLO 1 may position two or more frame groups using the same reference. In this case, for example, using the information of the infrared images included in each frame group, the amount of displacement of each image included in the frame group is detected. Each frame group includes the infrared image of the reference frame. First, with respect to the infrared images of one frame group, the control unit 50 detects the amount of displacement of the infrared images of another frame group. The amount of displacement is the amount of displacement between the frame groups. The control unit 50 then positions each frame group on the basis of the amount of displacement of each frame (namely, the value obtained by the displacement detection process). Further, the control unit 50 offsets the position of each image of the other frame group by the amount of displacement between the frame groups. As a result, the control unit 50 can position the fundus images included in two or more frame groups with respect to each other. In the present embodiment, after the positioning, the respective images are displayed side by side on the display 80.

Thereafter, S1 to S9 are repeatedly executed until an end instruction is input. When the end instruction is input, the control unit 50 ends the main process.

As described above, according to the present embodiment, the light separation unit 30 enables the three photo detectors 24, 26, and 28 to receive light of the different wavelength ranges. On the basis of the light reception signals from the photo detectors 24, 26, and 28, respectively, mutually different types of fundus images are generated. As a result, three types of fundus images based on the light of the mutually different wavelength ranges can be constructed.

In the present embodiment, the SLO 1 generates a maximum of three types of fundus images simultaneously (in parallel) by one frame of laser light scan. Thus, the generation and display of three types or more of images can be readily performed at a higher frame rate. As a result, the time required for the photographing can be decreased, for example. In addition, a live image can be easily displayed at a more preferable frame rate.

Further, the light separation unit 30 of the present embodiment causes the visible light of the three colors of blue, green, and red to be received by separate photo detectors. As a result, the fundus images based on the fundus reflected light of the visible light of blue, green, and red can be simultaneously generated. In addition, by combining the various colors of fundus images into one, a color fundus image can be obtained. On the basis of the simultaneously generated images, a live color image can be displayed in a preferable manner.

The light separation unit 30 of the present embodiment causes the fluorescence from the fundus and the fundus reflected light of the infrared range to be received by the separate photo detectors. As a result, the fluorescence image and the infrared image can be simultaneously generated.

Further, the SLO 1 of the present embodiment causes fluorescence to be simultaneously produced from two types of fluorescent material (fluorescein in the present embodiment) present in the fundus by the light from the laser light source 11. In this case, the light separation unit 30 causes the fluorescence emitted from the respective fluorescent materials to be received by the separate photo detectors. As a result, the SLO 1 can simultaneously generate two types of fluorescence images. Accordingly, for example, live images of two types of fluorescence images generated by the image generating units 61, 62, and 63 can be displayed side by side on the display 80. In addition, the two types of fluorescence images can be captured at one time. Accordingly, the burden of inspection on the examinee and the examiner can be limited when a plurality of types of fluorescence photography is performed.

Further, in the present embodiment, two types of fluorescence images and an infrared image can be simultaneously generated. Then, a live image of the two types of fluorescence images and a live image of the infrared image can be displayed side by side on the display 80.

The light separation unit 30 of the present embodiment separates, using the dichroic mirror 31 and the filter 33, the light of one of the blue/infrared wavelength range (the wavelength range corresponding to the fundus reflected light of the blue wavelength range and one of the fundus reflected light of the infrared range and the fundus fluorescence of the infrared range), the green/visible fluorescence wavelength range (the wavelength range corresponding to the fundus reflected light of the green wavelength range and the fundus fluorescence of the visible range), and the red/infrared wavelength range (the wavelength range corresponding to the fundus reflected light of the red wavelength range and the other of the fundus reflected light of the infrared range and the fundus fluorescence of the infrared range) with respect to the other two wavelength ranges, and further separates, using the dichroic mirror 32 and the filters 34 and 35, the light of the remaining two wavelength ranges. In this way, the photo detectors 24, 26, and 28 can receive the light of the blue/infrared wavelength range, the green/visible fluorescence wavelength range, and the red/infrared wavelength range separately. As a result, various types of image photography can be implemented as described above, such as the capturing of a color image, the independent/simultaneous capturing of an infrared fluorescence image and a visible fluorescence image, and the simultaneous capturing of a fluorescence image and an infrared image.

The fundus images generated by the SLO 1 may be individually handled. Of course, the images may be combined so as to generate a color image. Thus, the SLO 1 can provide the examiner with various information based on the generated images.

According to the present embodiment, the SLO 1 performs an image process on the infrared images captured at different timings so as to determine the amount of displacement between the infrared images. The SLO 1 detects the amount of displacement as the amount of displacement in a plurality of images captured simultaneously with the respective infrared images under a light receiving condition in the photo detectors 24, 26, and 28 different from that of the infrared images. As described above, the infrared image enables a high S/N ratio to be readily achieved. Further, the infrared image is not readily subject to a temporal change when angiography is performed, for example. Thus, the amount of displacement between the infrared images can be easily and accurately acquired. Between the infrared images and the images captured simultaneously with the infrared images, hardly any displacement is caused. Thus, by determining the amount of displacement using the infrared images, the amount of displacement of each simultaneously captured image can be easily and accurately obtained. For example, even in the case of an image having a large change depending on the time phase, such as a contrast fluorescence image, the amount of displacement can be accurately obtained. Accordingly, positioning of images can be accurately performed. In the case of an autofluorescence image, in order to improve the S/N ratio, an arithmetic mean image may be generated by determining an arithmetic mean of a plurality of autofluorescence images in a positioned state. In this case, the above-described positioning of the images using the amount of displacement can be accurately performed, whereby the number of the autofluorescence images used for the arithmetic mean image with a high S/N ratio can be limited. As a result, the time required for the capturing of the autofluorescence image can be decreased. Accordingly, the burden on the examiner and the examinee can be decreased.

While the embodiment has been described, the technology according to the present disclosure is not limited to the embodiments and may be variously modified.

For example, in the embodiment, the case has been described in which the light separation unit 30 includes a dichroic mirror and a filter. However, the configuration of the light separation unit 30 is not necessarily limited thereto. For example, the light separation unit 30 is disposed between the photo detectors 24, 26, and 28 and the examinee's eye E. The light separation unit 30 also includes a first wavelength separator that separates the light of the second wavelength range and the light of the third wavelength range from the light of the first wavelength range, and a second wavelength separator that separates the light of the second wavelength range and the light of the third wavelength range. The first wavelength separator corresponds to the dichroic mirror 31 and the filter 33 in the example of FIG. 1. The second wavelength separator corresponds to the dichroic mirror 32 and the filters 34 and 35 in the example of FIG. 1. The first wavelength separator is provided with a first optical path splitter that branches a first optical path from a common optical path of a second optical path and a third optical path. The second wavelength separator is provided with a second optical path splitter that branches the common optical path into the second optical path and the third optical path. The first optical path splitter corresponds to the dichroic mirror 31 in the example of FIG. 1. The second optical path splitter corresponds to the dichroic mirror 32 in the example of FIG. 1. In this case, an optical member that serves as both an optical path splitter and a wavelength separator, such as a dichroic mirror, may be used. Alternatively, the optical path splitter and the wavelength separator may be mutually independent optical members. An example of the optical path splitter other than the dichroic mirror is a beam splitter having no wavelength separating characteristics. Examples of the wavelength separator include various filters.

The wavelength ranges of the light that the light separation unit 30 causes the photo detectors 24, 26, and 28 to receive are not limited to those shown in FIG. 2 by way of example. For example, instead of the combination of the wavelength ranges received by the photo detectors 24, 26, and 28, the combinations shown in the tables of FIG. 11 and FIG. 12 may be used. By modifying the image generating unit that generates the image in each photographing mode as needed in accordance with the light received by the photo detectors, an operation similar to that of the embodiment can be implemented.

According to the embodiment, in the color photographing mode, a live image of an infrared image is acquired and displayed as the observation image, and a color image is acquired and displayed as the captured image. However, this does not suggest a limitation. For example, the color photographing mode may be a mode in which a color observation image is acquired and displayed. In this case, the control unit 50 may display a color live image as the observation image. In this case, the control unit 50 successively combines the three types of images of blue, green, and red successively acquired by the image generating units 61, 62, and 63, and displays the combined image as the observation image. In this case, the examiner can perform observation and the like of the examinee's eye E using the color image.

The SLO 1 may obtain a red-free image on the basis of at least one of the fundus image based on the blue fundus reflected light and the fundus image based on the green fundus reflected light. The red-free image is an image based on the fundus reflected light of red-free light (i.e., visible light that does not include the red wavelength range). The red-free image is useful, for example, for observation and diagnosis with regard to an optic nerve fiber. For example, one of the two types of fundus images may be used as the red-free image as is, or a combined image of the two types of images may be used as the red-free image.

According to the embodiment, the displacement of a plurality of the second fundus front images (fluorescence images in the embodiment) captured at different timings under mutually the same (single) light receiving condition is detected using the amount of displacement in the first fundus front image (an infrared image in the embodiment). However, this does not suggest a limitation, and the control unit 50 may detect the displacement of two or more types of second fundus front images captured under mutually different light receiving conditions that are different from the light receiving condition (the first light receiving condition) for the first fundus front image, using the amount of displacement in the first fundus front image. In this way, for example, the displacement between an autofluorescence image and a contrast fluorescence image, and the displacement between an infrared fluorescence image and a visible fluorescence image can be detected. For example, in the case of detecting the displacement between an autofluorescence image and a contrast fluorescence image, the displacement between the first fundus front images (such as infrared images) captured in association with each autofluorescence image and each contrast fluorescence image respectively is calculated by an image process. Then, the displacement of each first fundus front image is detected as the displacement of the autofluorescence image or the contrast fluorescence image captured in correspondence with the first fundus front image. As a result, for example, even between images having greatly different contents due to the difference in light receiving condition, the amount of displacement can be easily and accurately obtained. The displacement thus detected may be utilized for positioning two or more types of second fundus front images. Further, the images after positioning may be displayed side by side on the display 80. In this case, for example, the examiner can easily grasp corresponding locations of the two images having different light receiving conditions.

In the embodiment, the case has been described in which, as the first fundus front image as the reference for displacement detection of the second fundus front image, an infrared image by the fundus reflected light of the infrared range is utilized. However, this does not suggest a limitation. The control unit 50 may utilize the fundus image by the fundus reflected light of the visible range (such as the fundus image by the wavelength range of any of blue, green, and red) as the first fundus front image, for example. In this case, the control unit 50 may use both the fundus image by the fundus reflected light of the visible range and the infrared image as the first fundus front image. For example, the control unit 50, when positioning a color image and a red-free image with a fluorescence image, calculates the amount of displacement between the fundus image constituting the color image or the red-free image and relating to a color and the infrared image captured in association with the fluorescence image by an image process. Then, the displacement of each image is detected as the displacement of the image captured in correspondence with each image.

The control unit 50 may capture, at the time of visible fluorescence photography and infrared fluorescence photography, an image by the fundus reflected light other than infrared light in an associated manner, for example. The image by the fundus reflected light may be utilized for displacement detection and positioning with respect to a color image, for example. Thus, the control unit 50 can capture an image that is not used for fundus observation in an associated manner for displacement detection and the like.

In the embodiment, the second fundus front image captured in association with the first fundus front image has been the second fundus front image in which the light from each fundus is received simultaneously with the first fundus front image. However, there may be a time lag in the timing of detection of the light from each fundus. For example, when the first fundus front image and the second fundus front image are captured one by one alternately, the second fundus front image captured immediately before or after the capturing of the first fundus front image may be handled as the image captured in association with the first fundus front image.

In the embodiment, the case has been described in which the first fundus front image and the second fundus front image are captured on the basis of the light reception signals from different photo detectors. However, this does not suggest a limitation, and the first fundus front image and the second fundus front image may be captured on the basis of the light reception signal from the same photo detector. For example, there may be employed not only the configuration in which the first fundus front image and the second fundus front image are alternately captured, but also the configuration in which the first fundus front image and the second fundus front image are captured on the basis of the light reception signal from the same photo detector.

In the embodiment, the case has been described in which the amount of displacement of the fluorescence image is detected using the fundus front image (an infrared image in the embodiment) by the light of a different receiving condition from the fluorescence image. The image of which the amount of displacement is detected by the above technique is not necessarily limited to the fluorescence image.

In the embodiment, image positioning is performed when the captured image is displayed. However, the timing of the positioning is not necessarily limited to this. For example, the positioning may be performed immediately after the amount of displacement is detected.

After the positioning is completed, the displacement amount data used for the positioning may be deleted from the storage unit 51, whereby the capacity of the storage unit 51 can be used in a more preferable manner.

The displacement detection according to the embodiment may be applied to an image captured by an ophthalmic apparatus other than the scanning laser ophthalmoscope. For example, when a fluorescence image of the fundus front image and an infrared image are captured in association with each other by a fundus camera, and when the fluorescence images captured at different timings are subjected to displacement detection, the control unit 50 may obtain the displacement between the fluorescence images on the basis of a displacement calculated from the infrared image. The control unit 50, when capturing a color image (for example, immediately before or after the image is captured), may also capture an infrared image in association with the image, and determine a displacement between the color image and the fluorescence image on the basis of a displacement calculated from the infrared image.

The different photographing conditions may include conditions that are different in the light projecting condition and/or the photographing condition. In the above description, the case where the light receiving conditions are different has been mainly described. An example of different light projecting conditions may include using green excitation light to capture an autofluorescence image and using blue excitation light to capture an autofluorescence image.

In the embodiment, the case has been described in which displacement detection for a plurality of fundus front images is performed by the SLO 1 (the control unit 50). However, this does not suggest a limitation. For example, the detection of the amount of displacement may be performed by an image processing device separate from the SLO 1. The image processing device may be a processing device included in an ophthalmic apparatus separate from the SLO 1, or a general-purpose computer (such as a personal computer). The image processing device may be configured to determine the amount of displacement between at least two types of images of the first fundus front image and the second fundus front image that are transferred from the SLO 1.

In the present embodiment, the treatment apparatus (the control unit 50) may acquire the fundus front images from a storage unit provided in the processing apparatus or a server. Namely, the fundus front image acquisition technique may include a method by which an image captured by the ophthalmic photography apparatus is directly acquired, or a method by which an image once stored in the storage unit is acquired.

In the above description, the case has been described in which the displacement between the fundus front images captured by one fundus photography apparatus (such as the SLO 1) is detected. However, this does not suggest a limitation. For example, when a displacement is detected between the second fundus front images captured by different fundus photography apparatuses at different timings, the displacement between the first fundus front images captured in association by the apparatuses may be used. In this case, the first fundus front images are preferably images captured by an optical system having the same photographing condition.

In the above case, in a non-transitory storage medium (a hard disk and the like) having an image processing program to be executed by a processor of the image processing device stored therein, there may be prepared (stored) a program for causing the processor of the image processing device to execute the process of S6 or S6 to S8 of the displacement detection process executed by the SLO 1 of the embodiment. In this case, too, the displacement between images can be determined similarly to the case where the SLO 1 of the embodiment is used. The acquisition of the fundus front image is a concept that includes the acquisition of an image by the processor.

In the embodiment, while the SLO 1 has been described as being an SLO device that scans the observation surface with laser light two-dimensionally, this does not suggest a limitation. For example, the SLO 1 may be a so-called line scan SLO. In this case, on the basis of the operation of the scanning unit 16, the observation surface is one-dimensionally scanned with a line of laser light flux.

The scanning laser ophthalmoscope according to the present embodiment may include the following first to thirteenth scanning laser ophthalmoscopes.

The first scanning laser ophthalmoscope is provided with an irradiation optical system including a laser light source that outputs laser light and a laser light scanning unit for two-dimensionally scanning the fundus with the laser light; a light receiving optical system that receives, using a photo detector, light obtained from the fundus as a result of the laser light irradiation of the fundus by the irradiation optical system; and a processor that generates a fundus image on the basis of a light reception signal from the photo detector, wherein the light receiving optical system is provided with at least three of the photo detectors and a wavelength separator disposed in an optical path of the light receiving optical system so as to divide an optical path of the light obtained from the fundus into three branches, cause a first photo detector to receive the light of a first wavelength range, cause a second photo detector to receive light of a second wavelength range different from the first wavelength range, and cause a third photo detector to receive light of a third wavelength range different from the first wavelength range and the second wavelength range, and wherein the processor generates a first fundus image on the basis of the light reception signal from the first photo detector, a second fundus image on the basis of the light reception signal from the second photo detector, and a third fundus image on the basis of the light reception signal from the third photo detector.

The second scanning laser ophthalmoscope is according to the first scanning laser ophthalmoscope, wherein the laser light source outputs laser light including a blue wavelength range, a green wavelength range, and a red wavelength range, and the wavelength separator is disposed in the optical path of the light receiving optical system so as to cause one of three colors of fundus reflected light of the blue wavelength range, fundus reflected light of the green wavelength range, and fundus reflected light of the red wavelength range to be received by the first photo detector as the light of the first wavelength range, while simultaneously causing one of the three colors of the fundus reflected light other than the light received by the first photo detector to be received by the second photo detector as the light of the second wavelength range, and causing one of the three colors of the fundus reflected light other than the light received by the first photo detector and the second photo detector to be received by the third photo detector as the light of the third wavelength range.

The third scanning laser ophthalmoscope is according to the second scanning laser ophthalmoscope, wherein the processor combines the first fundus image, the second fundus image, and the third fundus image successively generated by the processor so as to generate a color live image which is a live image of a color fundus image, and causes the color live image to be successively displayed on a display.

The fourth scanning laser ophthalmoscope is according to the first scanning laser ophthalmoscope, wherein the laser light source outputs laser light having a wavelength range of excitation light for a first fluorescent material, and a wavelength range of excitation light for a second fluorescent material different from the first fluorescent material, wherein the wavelength separator is disposed in the optical path of the light receiving optical system so as to cause first fundus fluorescence emitted from the first fluorescent material to be received by one of the first photo detector, the second photo detector, and the third photo detector, while simultaneously causing second fundus fluorescence emitted from the second fluorescent material to be received by one of the other two photo detectors, and wherein the processor generates a first fundus fluorescence image which is a fundus image based on the first fundus fluorescence, and a second fundus fluorescence image which is a fundus image based on the second fundus fluorescence.

The fifth scanning laser ophthalmoscope is according to the fourth scanning laser ophthalmoscope, wherein the laser light source is such that the laser light includes a wavelength of an infrared range different from the wavelength ranges of the first fundus fluorescence and the second fundus fluorescence, the wavelength separator causes the fundus reflected light of the infrared range to be received by the photo detector different from the two of the first photo detector, the second photo detector, and the third photo detector that receive the first fluorescence or the second fluorescence, and the processor generates an infrared reflected image which is the fundus image based on the fundus reflected light of the infrared range.

The sixth scanning laser ophthalmoscope is according to the fourth or the fifth scanning laser ophthalmoscope, including a display control unit that causes the live image of the first fundus fluorescence image and the live image of the second fundus fluorescence image that are successively generated by the processor to be successively displayed side by side on the display.

The seventh scanning laser ophthalmoscope is according to one of the fourth to the sixth scanning laser ophthalmoscopes, including a light shielding portion for blocking the light of a wavelength range different from at least the wavelength range of the first fluorescence, the wavelength range of the second fluorescence, and the infrared range among the wavelength ranges of the laser light output from the laser light source, and an inserting/removing unit for inserting or removing the light shielding portion between the examinee's eye and the photo detectors.

The eighth scanning laser ophthalmoscope is according to the first scanning laser ophthalmoscope, wherein the laser light source outputs the laser light including a blue wavelength range, a green wavelength range, a red wavelength range, and an infrared range, wherein the wavelength separator is disposed in the optical path of the light receiving optical system so as to cause, when a color fundus image comprising red, blue, and green is to be acquired, one of the three colors of fundus reflected light of the blue wavelength range, the green wavelength range, and the red wavelength range to be received by the first photo detector as the light of the first wavelength range, while simultaneously causing one of the three colors of fundus reflected light other than the light received by the first photo detector to be received by the second photo detector as the light of the second wavelength range, and causing one of the three colors of fundus reflected light other than the light received by the first photo detector or the second photo detector to be received by the third photo detector as the light of the third wavelength range, and so as to cause, when a fluorescence fundus image is to be acquired, the fundus reflected light of the infrared range to be received by any of the first photo detector, the second photo detector, and the third photo detector, while simultaneously causing first fundus fluorescence generated when the laser light irradiates the first fluorescent material to be received by one of the first photo detector, the second photo detector, and the third photo detector which is different from the photo detector that receives the fundus reflected light of the infrared range.

The ninth scanning laser ophthalmoscope is according to the eighth scanning laser ophthalmoscope, wherein the wavelength separator is disposed in the optical path of the light receiving optical system so as to cause, when the fluorescence fundus image is acquired, second fundus fluorescence generated when the laser light irradiates a second fluorescent material different from the first fluorescent material to be received by one of the first photo detector, the second photo detector, and the third photo detector which is different from the two photo detectors that receive the fundus reflected light of the infrared range and the first fundus fluorescence.

The tenth scanning laser ophthalmoscope is according to any of the first to the ninth scanning laser ophthalmoscopes, wherein the wavelength separator is provided with a first wavelength separator that separates the light of the second wavelength range and the light of the third wavelength range with respect to the light of the first wavelength range, and a second wavelength separator that separates the light of the second wavelength range and the light of the third wavelength range.

The eleventh scanning laser ophthalmoscope is according to the tenth scanning laser ophthalmoscope, wherein the light receiving optical system includes a first optical path in which the first photo detector is disposed, a second optical path in which the second photo detector is disposed, and a third optical path in which the third photo detector is disposed, wherein the first wavelength separator is provided with a first optical path splitter that branches the first optical path with respect to a common optical path of the second optical path and the third optical path, and wherein the second wavelength separator is provided with a second optical path splitter that branches the common optical path to the second optical path and the third optical path.

The twelfth scanning laser ophthalmoscope is according to the tenth scanning laser ophthalmoscope, wherein the first wavelength separator is provided with a first optical path splitter having wavelength separating characteristics for reflecting and thereby guiding the light of the first wavelength range to the first optical path while transmitting the light of the second wavelength range and the light of the third wavelength range, and wherein the second wavelength separator is provided with a second optical path splitter having wavelength separating characteristics for reflecting and thereby guiding, of the light transmitted by the first optical path branch unit, the light of the second wavelength range is to the second optical path while transmitting and thereby guiding the light of the third wavelength range to the third optical path.

The thirteenth scanning laser ophthalmoscope is any one of the tenth to the twelfth scanning laser ophthalmoscopes, wherein the light of the first wavelength range, the light of the second wavelength range, and the light of the third wavelength range comprise light of mutually different wavelength ranges including: a blue/infrared wavelength range corresponding to the fundus reflected light of the blue wavelength range or one of the fundus reflected light of the infrared range and the fundus fluorescence of the infrared range; a green/visible fluorescence wavelength range corresponding to the fundus reflected light of the green wavelength range and the fundus fluorescence of the visible range; and a red/infrared wavelength range corresponding to the fundus reflected light of the red wavelength range and the other of the fundus reflected light of the infrared range and the fundus fluorescence of the infrared range, wherein the first wavelength separator causes the light of any of the blue/infrared wavelength range, the green/visible fluorescence wavelength range, and the red/infrared wavelength range to be separated with respect to the other two wavelength ranges, and the second wavelength separator causes the light of the other two wavelength ranges to be further separated.

According to the first to the thirteenth scanning laser ophthalmoscopes, the fundus image can be acquired in a preferable manner using a plurality of light receiving conditions.

The foregoing detailed description has been presented for the purposes of illustration and description. Many modifications and variations are possible in light of the above teaching. It is not intended to be exhaustive or to limit the subject matter described herein to the precise form disclosed. Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims appended hereto.

What is claimed is:

1. A scanning laser ophthalmoscope comprising:
   an irradiation optical system including a laser light source that outputs laser light and an optical scanner for two-dimensionally scanning fundus of an examinee's eye with the laser light;
   a light receiving optical system including first to third photo detectors that receive light obtained from the fundus as a result of the laser light irradiation of the fundus by the irradiation optical system; and
   a processor that generates a fundus image on the basis of a light reception signal from the photo detectors, wherein
   the light receiving optical system includes a wavelength separator disposed in an optical path of the light receiving optical system so as to branch an optical path of the light obtained from the fundus into three branches and cause the light of a first wavelength range to be received by the first photo detector, the light of a second wavelength range different from the first wavelength range to be received by the second photo detector, and the light of a third wavelength range different from the first wavelength range and the second wavelength range to be received by the third photo detector, and the processor generates a first fundus image on the basis of the light reception signal from the first photo detector, a second fundus image on the basis of the light reception signal from the second photo detector, and a third fundus image on the basis of the light reception signal from the third photo detector.

2. The scanning laser ophthalmoscope according to claim 1, wherein the laser light source outputs the laser light including a blue wavelength range, a green wavelength range, and a red wavelength range, and the wavelength separator is disposed in the optical path of the light receiving optical system so as to cause one of three colors of the fundus reflected light of the fundus reflected light of the blue wavelength range, the green wavelength range, and the red wavelength range to be received by the first photo detector as the light of the first wavelength range, cause one of the three colors of the fundus reflected light other than the light received by the first photo detector to be received by the second photo detector as the light of the second wavelength range, and cause one of the three colors of the fundus reflected light other than the light received by the first photo detector and the second photo detector to be received by the third photo detector as the light of the third wavelength range.

3. The scanning laser ophthalmoscope according to claim 2, wherein the processor generates a color live image which is a live image of a color fundus image by combining the first fundus image, the second fundus image, and the third fundus image successively generated by the processor, and causes the color live image to be successively displayed on a display.

4. The scanning laser ophthalmoscope according to claim 1, wherein the laser light source outputs the laser light including a wavelength range of excitation light for a first fluorescent material and a wavelength range of excitation light for a second fluorescent material different from the first fluorescent material, the wavelength separator is disposed in the optical path of the light receiving optical system so as to cause first fundus fluorescence emitted from the first fluorescent material to be received by any one of the first photo detector, the second photo detector, and the third photo detector, and to cause second fundus fluorescence emitted from the second fluorescent material to be received by one of the other two photo detectors, and the processor generates a first fundus fluorescence image which is a fundus image based on the first fundus fluorescence and a second fundus fluorescence image which is a fundus image based on the second fundus fluorescence.

5. The scanning laser ophthalmoscope according to claim 4, wherein the laser light source is such that the laser light includes a wavelength of an infrared range different from the wavelength ranges of the first fundus fluorescence and the second fundus fluorescence, the wavelength separator causes the fundus reflected light of the infrared range to be received by one of the first photo detector, the second photo detector, and the third photo detector which is different from the two photo detectors that receive the first fundus fluorescence or the second fundus fluorescence, and the processor generates an infrared reflect image which is a fundus image based on the fundus reflected light of the infrared range.

6. The scanning laser ophthalmoscope according to claim 4, wherein the processor causes a live image of the first fundus fluorescence image successively generated by the processor and a live image of the second fundus fluorescence image to be successively displayed side by side on the display.

7. The scanning laser ophthalmoscope according to claim 5, comprising:

a light shielding portion for blocking light of a wavelength range among the wavelength ranges of the laser light output from the laser light source which is different from at least the wavelength range of the first fundus fluorescence, the wavelength range of the second fundus fluorescence, and the infrared range; and an actuator for inserting or removing the light shielding portion between the examinee's eye and the photo detectors.

8. The scanning laser ophthalmoscope according to claim 1, wherein the laser light source outputs the laser light including a blue wavelength range, a green wavelength range, a red wavelength range, and an infrared range, and the wavelength separator is disposed in an optical path of the light receiving optical system so as to cause, when a color fundus image comprising red, blue, and green is to be acquired, one of the three colors of the fundus reflected light of the blue wavelength range, the green wavelength range, and the red wavelength range to be received by the first photo detector as the light of the first wavelength range, one of the three colors of the fundus reflected light other than the light received by the first photo detector to be received by the second photo detector as the light of the second wavelength range, and one of the three colors of the fundus reflected light other than the light received by the first photo detector or the second photo detector to be received by the third photo detector as the light of the third wavelength range, the wavelength separator causing, when a fluorescence fundus image is to be acquired, the fundus reflected light of the infrared range to be received by any of the first photo detector, the second photo detector, and the third photo detector, and causing first fundus fluorescence generated when the laser light irradiates a first fluorescent material to be received by one of the first photo detector, the second photo detector, and the third photo detector which is different from the photo detector that receives the fundus reflected light of the infrared range.

9. The scanning laser ophthalmoscope according to claim 8, wherein the wavelength separator is disposed in the optical path of the light receiving optical system so as to further cause, when the fluorescence fundus image is acquired, second fundus fluorescence generated when the laser light irradiates a second fluorescent material different from the first fluorescent material to be received by one of the first photo detector, the second photo detector, and the third photo detector which is different from the two photo detectors that receive the fundus reflected light of the infrared range and the first fundus fluorescence.

10. The scanning laser ophthalmoscope according to claim 1, wherein
the wavelength separator includes
a first wavelength separator that separates the light of the first wavelength range from the light of the second wavelength range and the light of the third wavelength range, and
a second wavelength separator that separates the light of the second wavelength range from the light of the third wavelength range.

11. The scanning laser ophthalmoscope according to claim 10, wherein
the light receiving optical system includes a first optical path in which the first photo detector is disposed, a second optical path in which the second photo detector is disposed, and a third optical path in which the third photo detector is disposed,
the first wavelength separator includes a first optical path splitter that branches the first optical path from a common optical path of the second optical path and the third optical path, and
the second wavelength separator includes a second optical path splitter that branches the common optical path into the second optical path and the third optical path.

12. The scanning laser ophthalmoscope according to claim 11, wherein
the first optical path splitter has wavelength separating characteristics for reflecting and thereby guiding the light of the first wavelength range to the first optical path while transmitting the light of the second wavelength range and the light of the third wavelength range, and
the second optical path splitter has wavelength separating characteristics for reflecting and thereby guiding, of the light transmitted by the first optical path splitter, the light of the second wavelength range to the second optical path while transmitting and thereby guiding the light of the third wavelength range to the third optical path.

13. The scanning laser ophthalmoscope according to claim 10, wherein:
the light of the first wavelength range, the light of the second wavelength range, and the light of the third wavelength range comprise light of mutually different wavelength ranges including
a blue/infrared wavelength range corresponding to the fundus reflected light of the blue wavelength range and one of the fundus reflected light of the infrared range and the fundus fluorescence of the infrared range,
a green/visible fluorescence wavelength range corresponding to the fundus reflected light of the green wavelength range and the fundus fluorescence of the visible range, and
a red/infrared wavelength range corresponding to the fundus reflected light of the red wavelength range and the other of the fundus reflected light of the infrared range and the fundus fluorescence of the infrared range;
the first wavelength separator separates the light of any of the blue/infrared wavelength range, the green/visible fluorescence wavelength range, and the red/infrared wavelength range from the other two wavelength ranges; and
the second wavelength separator separates the light of the other two wavelength ranges from each other.

* * * * *